(12) United States Patent
Van Holen et al.

(10) Patent No.: US 12,402,846 B2
(45) Date of Patent: Sep. 2, 2025

(54) IMAGING APPARATUS FOR IMAGING EX-VIVO TISSUE SPECIMENS

(71) Applicant: XEOS MEDICAL NV, Ghent (BE)

(72) Inventors: Roel Van Holen, Melsen (BE); Vincent Keereman, Ghent (BE); Jared W. Moore, Ghent (BE)

(73) Assignee: XEOS MEDICAL NV, Ghent (BE)

( * ) Notice: Subject to any disclaimer, the term of this patent is extended or adjusted under 35 U.S.C. 154(b) by 230 days.

(21) Appl. No.: 18/261,349

(22) PCT Filed: Jan. 21, 2022

(86) PCT No.: PCT/EP2022/051340
§ 371 (c)(1),
(2) Date: Jul. 13, 2023

(87) PCT Pub. No.: WO2022/157305
PCT Pub. Date: Jul. 28, 2022

(65) Prior Publication Data
US 2024/0074714 A1 Mar. 7, 2024

(30) Foreign Application Priority Data
Jan. 22, 2021 (EP) .................................. 21153099

(51) Int. Cl.
*A61B 6/03* (2006.01)
*A61B 6/00* (2024.01)
*A61B 6/42* (2024.01)

(52) U.S. Cl.
CPC .............. *A61B 6/032* (2013.01); *A61B 6/037* (2013.01); *A61B 6/4258* (2013.01); *A61B 6/4417* (2013.01); *A61B 6/5235* (2013.01)

(58) Field of Classification Search
CPC ....... A61B 6/032; A61B 6/037; A61B 6/4258; A61B 6/4417; A61B 6/5235; A61B 2090/374; A61B 2090/3762; A61B 6/03; G01T 1/1611
See application file for complete search history.

(56) References Cited

U.S. PATENT DOCUMENTS

2008/0048124 A1   2/2008  Pang et al.
2014/0198893 A1*  7/2014  Badawi ............... G01N 23/046
                                                         378/19

FOREIGN PATENT DOCUMENTS

JP    2009183448 A    8/2009
WO    2021108742 A1   6/2021

OTHER PUBLICATIONS

Goker, Menekse et al., "18F-FDG micro-PET/CT for intraoperative margin assessment during breast-conserving surgery", Acta Chirurgica Belgica, vol. 120, No. 5, Sep. 2, 2020, pp. 366-374.
Extended European Search Report from corresponding European Patent Application No. EP21153099.3, Jul. 13, 2021.
International Search Report from corresponding PCT Application No. PCT/EP2022/051340, Apr. 20, 2022.

* cited by examiner

*Primary Examiner* — Courtney D Thomas
(74) *Attorney, Agent, or Firm* — Workman Nydegger

(57) ABSTRACT

An imaging apparatus for imaging ex-vivo tissue specimens includes a positron emission tomography imaging module having at least one pair of PET detectors; a computed tomography imaging module including an X-ray source and an X-ray detector; a tissue specimen receiving element configured to receive the tissue specimen to be imaged.

15 Claims, 2 Drawing Sheets

IMAGING APPARATUS FOR IMAGING EX-VIVO TISSUE SPECIMENS

FIELD OF THE INVENTION

The present invention generally relates to an imaging apparatus for imaging ex-vivo tissue specimens including a positron emission tomography (PET) imaging module as well as an X-ray computed tomography (CT) imaging module.

BACKGROUND OF THE INVENTION

In the field of ex-vivo tissue specimen analysis, an important issue is the evaluation of resection accuracy. After resecting for example tumorous tissues, the surgical margins of the resected tissues need to be assessed in order to be able to decide whether more tissue has to be resected or not since tumorous tissues need to be removed as completely as possible. Thereto, the resected tissues need to have a sufficient margin of tumour free tissues. Such an evaluation of resection accuracy may be done by a histopathologist. However, the presence or stand-by of a histopathologist during an operation may be relatively expensive and may be logistically relatively difficult to achieve. At the same time, the histopathological evaluation may be a relatively time-consuming process and may be difficult to realize intraoperatively. Therefore, such a histopathological evaluation is rarely performed intraoperatively, resulting in an undesirable scheduling of additional subsequent surgeries in case of post-surgical detection of tumorous margins in the resected tissues.

It is known to use one or more imaging techniques in the evaluation of resection accuracy of ex-vivo tissue specimen, which imaging techniques can visualize tumorous tissue. A CT imaging module can for example detect differences in tissue densities in a tissue specimen and provide morphological information on the imaged tissue specimen, distinguishing tumorous tissue from healthy tissue. However, the contrast between tumorous and healthy tissue is often limited in CT images. A PET imaging module can detect the distribution of a positron-emitting radiotracer, administered to a patient before imaging, in the body of said patient. As some radiotracers are taken up in tumorous tissue with high specificity, a PET imaging module can for example provide images of tumorous tissue with a relatively high accuracy. Unfortunately, PET images may not provide detailed morphological information. Combining images made by a CT imaging module and by a PET imaging module can therefore be very advantageous in clinical imaging, in particular in margin assessment of a resected tissue specimen.

However, both a CT imaging module and a PET imaging module are rather voluminous and bulky devices and may be difficult to place and be operated within an operating room. When CT imagers and PET imagers are combined, the resulting device may even be bulkier. Spatial resolution of available PET and CT imagers may not enable accurate visualization of tumorous tissue in relatively small resected specimen. At the same time, such devices combining CT imagers and PET imagers are generally relatively complicated systems from a mechanical point of view because they need to combine restrictions imposed by CT imagers and by PET imagers. CT imagers may usually be configured to rotate around the specimen or subject to be imaged. Some combined CT-PET imaging devices may also require implantation of a lesion marker before performing imaging, which is a disadvantage of such systems.

It is therefore an aim of the present invention to solve or at least alleviate one or more of the above-mentioned problems. In particular, the invention aims at providing an imaging apparatus for imaging ex-vivo tissue specimens allowing intraoperative evaluation of resection accuracy of the tissue specimens.

SUMMARY OF THE INVENTION

To this aim, according to a first aspect of the invention, there is provided an imaging apparatus for imaging ex-vivo tissue specimens characterized by the features of claim 1. In particular, the apparatus comprises a positron emission tomography (PET) imaging module including at least one pair of PET detectors, a computed tomography (CT) imaging module including an X-ray source and an X-ray detector, and a tissue specimen receiving element configured to receive the tissue specimen to be imaged. In an inventive way, the apparatus further comprises a motion system configured to move the tissue specimen receiving element from the CT imaging module to the PET imaging module, the PET imaging module being located above or below the CT imaging module. This vertical configuration of the CT imaging module and the PET imaging module can provide a relatively compact imaging apparatus. The wording 'imaging apparatus' is to be understood in the present context as a single device, preferably a modular device, and not as a system comprising separate devices. Since the imaging apparatus according to the present invention can be made relatively compact and relatively lightweight, the apparatus can be used in an operating room, for example intraoperatively, i.e. during surgery.

The PET imaging module is preferably located above the CT imaging module. By placing the PET imaging module above the CT imaging module, the former can help in shielding an environment from potentially harmful radiation emitted by the CT imaging module. As a consequence, the CT imaging module itself can include a relatively light shielding since part of the shielding is done by the PET imaging module, which is advantageous for the imaging apparatus in terms of total weight. As an example, the CT imaging module can preferably be located in a substantially central position of the imaging apparatus, while the PET imaging module is located in a top part of the imaging apparatus.

The tissue specimen receiving element may for example be a transparent holder for holding an excised tissue specimen, or any other known specimen container or cassette, having an upstanding sidewall. Such an upstanding sidewall may help to keep the tissue specimen within a predefined border adapted to a field of view of one or each of the CT imaging module and PET imaging modules. A top side may be open or closable. The tissue specimen receiving element may also be a plate-like element, with or without an upstanding border.

A top side of the imaging apparatus can preferably include an opening configured to allow loading of the tissue specimen on the tissue specimen receiving element, said opening being closable by a lid. The opening can provide a gantry to the tissue specimen receiving element. The tissue specimen receiving element may be removable from the apparatus via said opening for loading the tissue specimen, and/or the tissue specimen may be loaded through the opening while the tissue specimen receiving element is within the imaging apparatus. Top side access to the tissue specimen receiving element may facilitate handling of the tissue specimen, in particular when a height of the imaging apparatus is substantially similar to a table height, in particular between more or less 80 cm and substantially 120 cm. Alternatively, access to the tissue specimen receiving element may be otherwise provided, for example via an opening in a side of the apparatus. The opening is closable by a lid. This lid can then help in the shielding of an environment from radiation emitted by one of the imaging modules of the imaging apparatus. Since the PET imaging module is above the CT imaging module and helps in shielding, the lid can be a relatively light weight lid. The lid or door can for example be a hinged lid or a sliding door, which may be closable manually or automatically after having provided the tissue specimen to be imaged to the tissue specimen receiving element. Any other known closable lid may also be used.

The lid can advantageously include a camera configured to provide top view images of the tissue specimen receiving element. The camera can preferably be an optical camera. Images of the tissue specimen placed on the tissue specimen receiving element can help in determining an orientation of the tissue specimen on the tissue specimen receiving element. An orientation of the tissue specimen may also be determined otherwise, for example by wires attached to the tissue specimen after resection, by specimen staining or by other known techniques, or any combination thereof.

The imaging apparatus can further comprise a substantially vertical bore configured to receive the tissue specimen receiving element and allowing movement of the tissue specimen receiving element within the substantially vertical bore. The vertical bore can allow the construction of a relatively compact imaging apparatus. The vertical bore preferably extends from the opening included in the top side of the imaging apparatus through the PET imaging module and down to the CT imaging module allowing movement of the tissue specimen receiving element within the substantially vertical bore from the opening to the CT imaging module and to the PET imaging module in a relatively simple and fluent movement.

The motion system may be configured to allow substantially vertical movement and/or rotational movement around a substantially vertical axis of the tissue specimen receiving element. In particular, the motion system can preferably be limited to allow a one-dimensional substantially vertical movement and/or a rotational movement around said same substantially vertical axis. The substantially vertical movement can for example allow moving the tissue specimen receiving element from a tissue specimen reception position, for example at a top side of the apparatus, to an imaging position within the CT imaging module, and further on to an imaging position within the PET imaging module. In the imaging position, for example in the CT imaging module, the motion system may be configured to rotate the tissue specimen receiving element, for example over 180° or more or less, allowing imaging of the tissue specimen over various angles. The motion system may further be configured to allow the substantially vertical movement in combination with the rotational movement around a substantially vertical axis of the tissue specimen receiving element resulting in a helical movement of the tissue specimen receiving element, which may be beneficial for helical acquisition of data, for example by the CT imaging module. As such, high quality imaging can be performed with a relatively simple mount including only one axis of movement.

The motion system can include a kinematic mount. A kinematic mount is a mount in which all degrees of freedom of a 3D object are restrained from moving preferably without over-constraint. In particular, the movable frame, such as the tissue specimen receiving element, may be supported by a ball bearing. Such a kinematically determined mount can simplify an alignment of the tissue specimen receiving element within the vertical bore and may diminish or obviate a need for recalibration after servicing the apparatus.

The motion system may be configured to perform a settling of the tissue specimen in the tissue specimen receiving element, for example by performing a shaking movement on the tissue specimen receiving element. The shaking movement may for example include a relatively quick downward movement followed by a relatively short upward movement, or the opposite, once or in a repetitive way. Many other settling movements may be possible. Such a settling movement may be performed after reception of the tissue specimen and before data acquisition by one of the imaging modules. The settling movement may be beneficial to avoid movement of the tissue specimen in the tissue specimen receiving element between data acquisition by the CT imaging module and the PET imaging module, which would hamper combination and/or comparison of data acquired by each of the imaging modules.

The PET imaging module is preferably a high-resolution PET imaging module having a spatial resolution below 3 mm, preferably below 2 mm, more preferably below 1 mm. The high-resolution PET imaging module preferably includes a monolithic scintillator, which can provide up to sub-millimeter spatial resolution in three dimensions. Alternatively, the PET imaging module can include an array of scintillating crystals. The PET imaging module preferably includes a ring of a plurality of PET detectors, for example including more than 5 PET detectors, for example more than 9 PET detectors, for example including 11 PET detectors or even more. Said PET detectors are preferably PET detectors using silicon photomultipliers.

The CT imaging module can be a micro-CT imaging module having a spatial resolution below 0.2 mm (below 200 µm), more preferably below 0.1 mm (below 100 µm). The CT imaging module can for example be a cone beam CT scanner including a microfocus X-ray source and a large area flat panel X-ray detector. The X-ray detector can include CMOS image sensors coupled with a scintillator. Other configurations for the CT imaging module are possible.

A shielding of the CT imaging module can be a lead-free shielding. It is known that CT imagers emit potentially harmful radiation, from which an environment of the imagers need to be shielded. This shielding can generally comprise an enclosure of the CT imaging module, which enclosure usually includes lead. The high density of lead can make it a useful shield against X-ray and gamma-ray radiation. Due to environmental risks of lead disposal, it may be preferred to provide a lead-free shielding, which can include a steel or steel alloy. A steel shielding may be thicker than a corresponding shielding including lead, but a steel shielding is relatively easy to manufacture.

The imaging apparatus can further comprise an image reconstruction module configured to perform image reconstruction based on data from the PET imaging module and/or from the CT imaging module. The image reconstruction module can provide a reconstructed image based on data from the CT imaging module alone or based on data from the PET imaging module alone. The image reconstruction module is preferably also configured to provide a reconstructed image based on data from both the CT imaging module and the PET imaging module. The relatively high sensitivity of the PET and CT imaging modules can reduce acquisition time by the imaging modules and allow a relatively rapid start of image reconstruction. The image reconstruction module is preferably configured to provide reconstructed images within more or less 15 minutes, more preferably within more or less 10 minutes. Alternatively, the image reconstruction could be performed remotely, for example by an image reconstruction module on a remote computing module or server.

The image reconstruction module may be configured to perform 3D image reconstruction. 3D imaging may be advantageous to remove a sampling bias. Additionally, the CT imaging module may be configured to perform circular or helical scanning of the tissue specimen to provide a plurality of images from different viewpoints.

The imaging apparatus may further comprise a user interface. The user interface may for example comprise a screen, which may be configured to show the images provided by the image reconstruction module. The screen may for example be located on the top side of the imaging apparatus, or elsewhere. The screen may be a touch screen or any other type of screen. The user interface may further comprise a plurality of buttons, handles or pedals configured to allow a user to operate the imaging apparatus in a relatively easy way with a minimum of actions to be performed: a starting button or pedal may for example open the opening giving access to the tissue specimen receiving element. The user interface can for example also include a visual means, such as for example a LED strip or any other known means, configured to indicate progress of the process of scanning of the tissue specimen by the CT imaging module and the PET imaging module.

The imaging apparatus can advantageously be a mobile apparatus. It is preferred that the imaging apparatus includes wheels, in particular swivel wheels, allowing easy moving of the imaging apparatus. Such a mobile imaging apparatus can, in particular, be advantageous for use in an operating room, where the imaging apparatus can then relatively easily be drawn near the operating table when needed and be put aside before and afterwards. Other known moving means than wheels can be contemplated as well.

According to a second aspect of the invention, there is provided a method to perform ex-vivo tissue specimens imaging having the features of claim 15. Such a method can provide one or more of the above-mentioned advantages.

In a preferred embodiment, the method may include a step of injection of a radiotracer into the tissue. An example of such a radiotracer is 18F-fluorodeoxyglucose, commonly known as FDG, a glucose analogue which is taken up into cells that are metabolically active, such as for example tumor cells. FDG has a radioactive decay time of more or less 110 min. Other isotopes which can be used in PET imaging include for example C-11 having a decay time of more or less 20 minutes, or 68-Gallium having a decay time of more or less 68 minutes. These isotopes can be linked to other molecules (which then become radiotracers), such as PSMA. Other molecules, such as nanobodies, can also be linked to PET-isotopes. To optimize PET imaging an optimal time window for administration of the radiotracer can be calculated, taking into account the radioactive decay time and an absorption or uptake time of the tracer by the body. It is generally recommended to have an interval in a range of more or less 60 to 90 minutes between the administration of the radiotracer and the imaging, although even after more or less 30 minutes, there may already be a relatively strong uptake of the radiotracer in target cells of the tissue. Too early administration of the radiotracer can lead to a relatively important loss of signal and reduced image quality. Administering a higher dose of the radiotracer to compensate for an early administration can increase radiation load.

It is preferred that the step of administration of a radiotracer is performed before excision of the tissue specimen from a patient. In this way, the imaging of the ex-vivo tissue specimen can be performed immediately after excision of the tissue specimen without having to wait for uptake of the radiotracer by the specimen. Alternatively, the radiotracer can be injected into the ex-vivo tissue specimen.

It may be preferred that the step of administration of the radiotracer is performed intraoperatively, i.e. during surgery of a patient, when the patient is preferably under general anaesthetic. More preferably, the step of administering the radiotracer is performed before section of any vasculature of the patient. In this way, the radiotracer can circulate well inside the body and be taken up by the target tissue. Such a method can allow to decrease the administered dose of the radiotracer while optimizing uptake time by the body before imaging of excised tissue specimen, resulting in improved image quality. This method may in particular be advantageous for surgeries which take relatively long. Such a method may be considered as an invention per se.

DETAILED DESCRIPTION OF EMBODIMENT(S)

Figure 1:
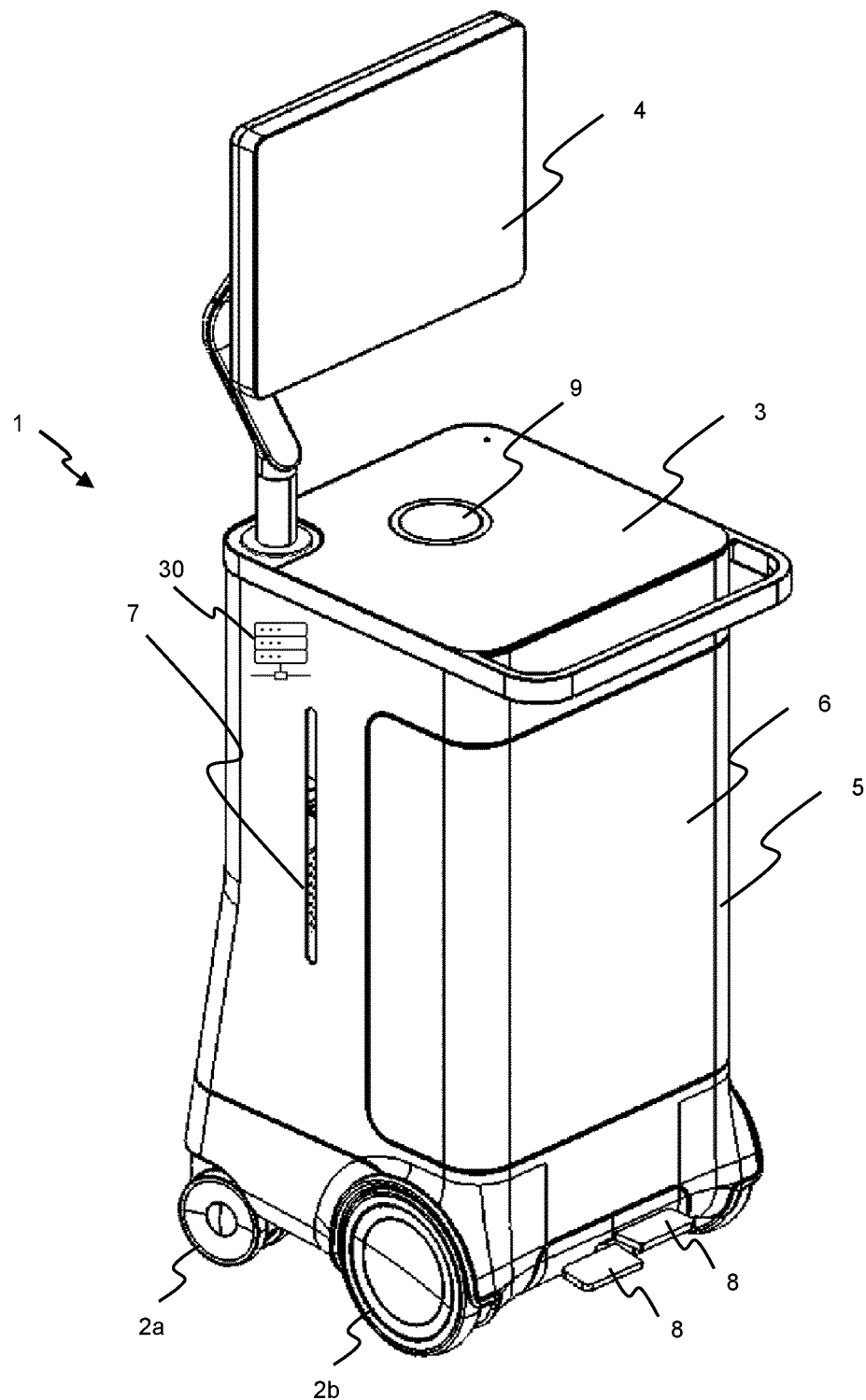
FIG. 1 shows a perspective view on a preferred embodiment of an imaging apparatus for imaging ex-vivo tissue specimens according to a first aspect of the invention.

FIG. 1 shows a perspective view on a preferred embodiment of an imaging apparatus 1 for imaging ex-vivo tissue specimens according to a first aspect of the invention. The imaging apparatus 1 is preferably a mobile apparatus. It can include at least two wheels, preferably four wheels, which may be swivelling wheels 2a or non-swivelling wheels 2b. In this way, the imaging apparatus 1 can be easily moved to and moved around within an operating theatre. The apparatus 1 can for example be approached near an operating table so that an excised tissue specimen can be inserted into the imaging apparatus 1 for imaging and margin assessment intraoperatively. A top side 3 of the imaging apparatus 1 may be located at table-height, for example at a height between more or less 80 cm to approximately 120 cm from a floor. The imaging apparatus 1 may include a user interface, such as for example a display 4, which may be removably or fixedly attached to a top side 3 of the imaging apparatus 1 or in any other way. The display 4 can preferably be rotated into various directions so that practitioners in the operating theatre can easily visualize results displayed on the screen of the display 4. The user interface can further include an input element configured to allow input of data into the imaging apparatus. The input element may be one of a keyboard, a mouse, a touch screen, or any other input element. A touch screen may for example be included in a top side 3 of the apparatus 1, for example to allow input of patient data or any other information. The imaging apparatus 1 can comprise an image reconstruction module 30 configured to perform image reconstruction based on data from the PET imaging module and/or from the CT imaging module. The image reconstruction module is preferably configured to perform 3D image reconstruction. The image reconstruction module 30 can comprise a suitable computing system enabling the performance of image reconstruction. The computer system is preferably included in the imaging apparatus 1. The computer system may include a wired or wireless communication interface for communicating with a remote computing system, for example with a hospital computing system to store results. Alternatively, image reconstruction may be performed on a remote computing system.

At least one side, preferably a front side 5 of the imaging apparatus 1, can include an access to an inside of the imaging apparatus 1 to allow relatively easy maintenance of the different modules within the imaging apparatus 1. Said access may be closable by a lid or a door 6. A side of the imaging apparatus 1 may further include a progress indicator, for example a lighting strip 7, preferably including a plurality of LED lights, preferably extending in a row, which may be configured to indicate progress of the imaging process of a tissue specimen. The one or more progress indicators, such as the lighting strip 7, can preferably be placed at a distance of the user interface, in particular at a distance of the display 4. Progress of the imaging process may be indicated by a colour of light, by an intensity of light, by a duration of lighting, by a number of lights, by glowing, flickering, blinking of light and/or by any combination of these. The lighting strip 7 may for example be configured to emit blue, green, red and/or yellow light or more or fewer colours, over part of the strip and/or over the entire strip, in a steady way, in a blinking way, or in any other way. Each of these lighting properties, or any combination of these properties, may correspond to a step of the imaging process and/or for an evaluation of a step, for example to the opening of a lid of the imaging apparatus, to the start and/or progress of the imaging by the CT imaging module or to the moving of the tissue specimen receiving element, or any other step of the imaging process. A specific colour or way of lighting of the lighting strip 7 may also be used as a warning, for example when a lid 6 of the imaging apparatus is open and/or when X-rays are being emitted. Any other progress indicator may be used alternatively. One or more progress indicators, such as the lighting strip 7, may also be placed on a different side of the imaging apparatus 1, for example one on each side of the imaging apparatus 1. In this way, a user, such as a surgeon, can remain near a patient, at a distance of the imaging apparatus, while being able to follow the progress of the imaging process and being warned when intervention from his side is required. The imaging apparatus 1 can further include operating pedals 8 to facilitate operation of the apparatus 1 in a sterile environment of an operating theatre. The pedals may for example operate a brake on the wheels 2a, 2b. A top side 3 of the imaging apparatus 1 can include an opening 9 configured to allow loading of the tissue specimen on a tissue specimen receiving element. The opening 9 is preferably closable by a lid (not shown), or by any other type of closing element. A top side 3 of the imaging apparatus 1 may include a further progress indicator, for example of a substantially circular shape, for example around the opening 9. Said further progress indicator can also be a lighting strip, preferably including a plurality of LEDs, and can be configured to function independently from and/or in combination with the lighting strip 7, which can increase the number of messaging and/or warning possibilities through a combination of colours, timing and other lighting properties. The lid, in particular an inner side of the lid facing towards an inner side of the imaging apparatus 1, can include a camera configured to provide top view images of the tissue specimen receiving element. An operating pedal 8 can for example be configured to open the lid closing off the opening 9 so that an operator can put the tissue specimen into the tissue specimen receiving element without touching anything. The same or another pedal 8 may be configured to initiate an imaging procedure. Alternatively, the lid may be opened and/or closed automatically in an automated workflow. An imaging procedure may also be initiated by a touch screen included in the top side 3 of the imaging apparatus 1.

Figure 2:
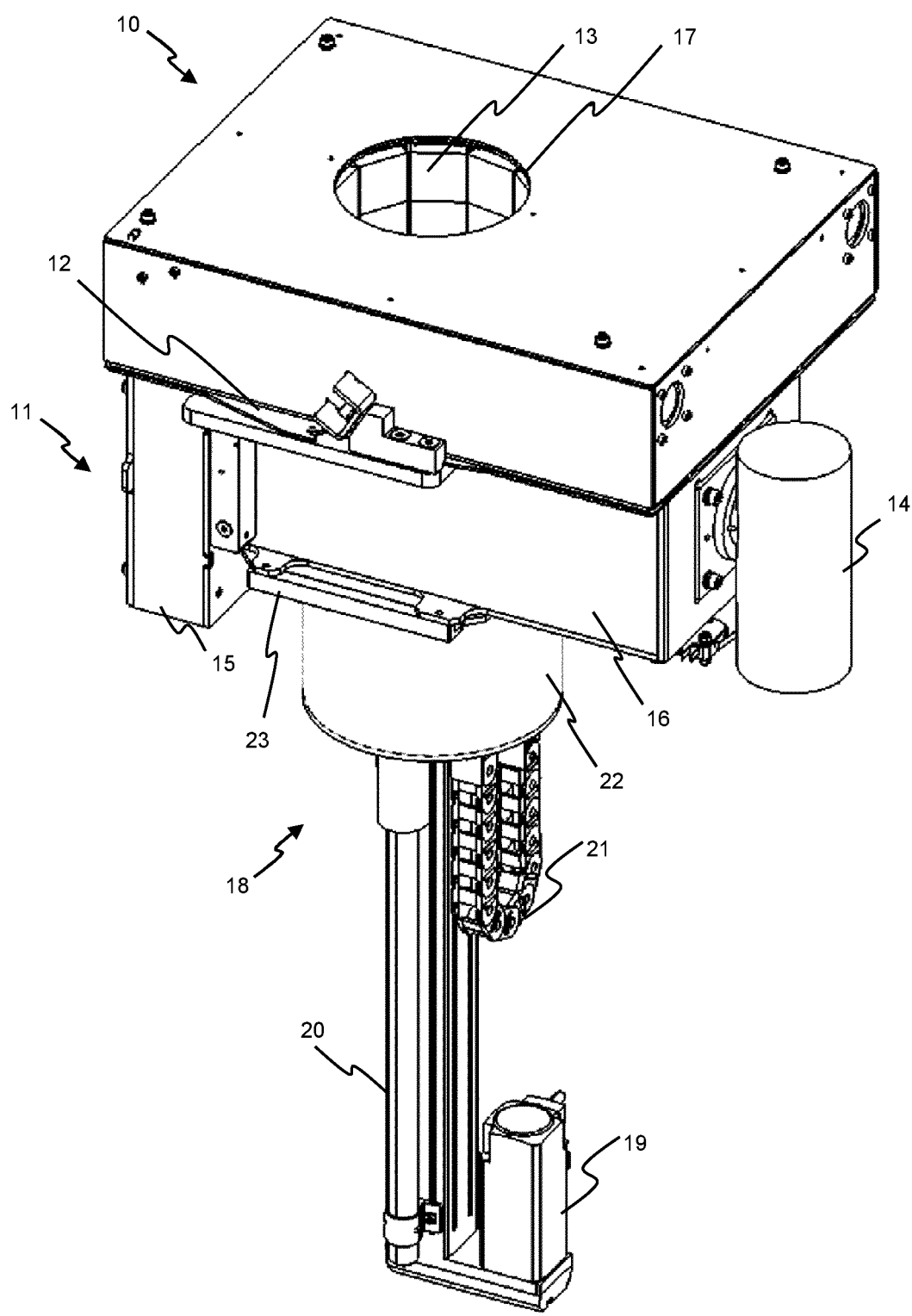
FIG. 2 shows a perspective view on an inside of the imaging apparatus shown in FIG. 1.

FIG. 2 shows a perspective view on an inside of the imaging apparatus 1 shown in FIG. 1. The imaging apparatus 1 comprises a positron emission tomography (PET) imaging module 10 and a computed tomography (CT) imaging module 11. The PET imaging module 10 is located above the CT imaging module 10. In the present embodiment, the PET imaging module 10 is even mounted directly on top of the CT imaging module 10 via a dedicated mount 12, for example including bolts or any other suitable fixation element. The mount 12 may advantageously include releasable fixation elements to provide a modular system in which every module is individually replaceable. Thanks to the mounting of the PET imaging module 10 above the CT imaging module 11, the PET imaging module 10 can contribute to an efficient shielding of the CT imaging module 11 allowing use of relatively light-weight shielding material enclosing the CT imaging module 11. The PET imaging module 10 can comprise a ring of PET detectors 13, preferably silicon-photomultiplier-based PET detectors 13. The PET imaging module 10 is preferably configured to be used with the 18F-FDG radiotracer, which is commonly used in cancer detection, and is particularly fit for margin assessment of ex-vivo tissue. The PET imaging module 10 is a high-resolution PET imaging module having a spatial resolution preferably below 1 mm. The CT imaging module 11 is a micro-CT imaging module preferably having a spatial resolution below 0.2 mm. The CT imaging module 11 includes an X-ray source 14, for example a microfocus X-ray source, and an X-ray detector 15, for example a large area flat panel X-ray detector. The X-ray detector 15 can include CMOS image sensors coupled with a scintillator. A CT imaging module 11 is generally enclosed in a protective shielding 16 to protect an environment of the CT imaging module 11 from potentially harmful radiation. The shielding 16 of the CT imaging module can for example be a lead-free shielding.

The imaging apparatus 1 preferably comprises a substantially vertical bore 17 configured to receive the tissue specimen receiving element and allowing movement of the tissue specimen receiving element within the substantially vertical bore 17. The vertical bore 17 is preferably substantially vertically aligned with the opening 9 in the top side 3 of the imaging apparatus 1. The substantially vertical bore 17 preferably crosses the PET imaging module 10 and the CT imaging module 11 such that the tissue specimen receiving element can be moved substantially vertically between said opening 9, the PET imaging module 10 and the CT imaging module 11. The imaging apparatus 1 further comprises a motion system 18 configured to move the tissue specimen receiving element from the CT imaging module 11 to the PET imaging module 10, preferably from the opening 9 through the substantially vertical bore 17 to the CT imaging module 11 and to the PET imaging module 10 and back to the opening 9. Thereto the motion system 18 can include a linear motor 19, linear motion guides 20, and a cable carrier 21 for protecting cables. The linear motor can be configured to linearly move the tissue specimen receiving element the movement being guided by the linear motion guides 20. The motion system 18 can for example include a kinematic mount (not shown), in which a set of three, or even a set of six, ball bearings are constrained by corresponding conical recesses, providing a solid mounting which can avoid time consuming readjustments after maintenance of the apparatus. The kinematic mount may for example be located on top of the motion system 18 and may be connected with a lower side of the CT imaging module 11. After loading of the tissue specimen in or on the tissue specimen receiving element, the motion system may be configured to perform a settling movement, for example a downward movement in the vertical bore including a relatively important acceleration, followed by a sudden halt of the movement. Other movements are possible as well, for example a shaking movement. Acceleration and deceleration forces on the tissue specimen can then result in settling the tissue specimen so that the tissue specimen will be immobile within the tissue specimen receiving element during the imaging by both the CT imaging module 11 and the PET imaging module 10. The motion system 18 may further be configured to allow rotational movement around a substantially vertical axis of the tissue specimen receiving element. Thereto the motion system 18 can include a rotary motor 22 configured to have the tissue specimen receiving element rotate around a central vertical axis. Such a rotational movement of the tissue specimen receiving element can allow the CT imaging module to make a plurality of images of the tissue specimen from different angles, for example from various angles distributed over a full 360° or less despite a fixed mount of the CT imaging module 11. The motion system 18 may also be configured to combine a linear movement and a rotational movement into a helical movement of the tissue specimen receiving element, in particular through the CT imaging module 11. In the present embodiment, the CT imaging module 11 is mounted on the motion system 18, in particular on the rotary motor 22, via a dedicated mount 23 which can for example include bolts or other suitable fixing means. The CT imaging module 11 is preferably releasably mounted onto the rotary motor 22.

During surgery, for example during breast surgery, the imaging apparatus 1 may be used to perform ex-vivo tissue specimen imaging. Thereto, a surgeon, or more preferably a nurse, may move the imaging apparatus 1 near the operating table. A lid may be removed from the opening 9, preferably hands-free, for example automatically after initiation of an automated workflow, or manually. The surgeon or the nurse may put the excised tissue specimen on or in the tissue specimen receiving element. The tissue specimen receiving element can then be provided to the vertical bore 17 via the opening 9. A top end of the vertical bore 17 may be shaped such as to correctly position the tissue specimen receiving element in the vertical bore 17. Next, the motion system 18 may move, for example lower, the tissue specimen receiving element such that the lid over the opening 9 can be closed again. Alternatively, the tissue specimen receiving element may be located just below the lid configured to cover opening 9. A camera, which may be mounted to an inside of said lid, may now make top view images of the tissue specimen. Alternatively, said camera may record at least part of the imaging procedure in the imaging apparatus 1. The motion system 18 may then perform a settling movement, such as for example a fast downward movement followed by a short upward movement, or for example a shaking movement, to settle down the tissue specimen in the tissue specimen receiving element. Then the motion system 18 may move the tissue specimen receiving element to the CT imaging module 11. The CT imaging module then performs imaging of the ex-vivo tissue specimen, preferably by helical scanning, for example by a helical movement of the tissue specimen receiving element through the CT imaging module 11. The image reconstruction module 30 can preferably start image reconstruction immediately. Already during scanning, some CT images may be displayed relatively quickly in a 2D preview mode, so without image reconstruction, on the display 4, for example the first image and a further image taken from a 90° angle with respect to the first image. In this way, a surgeon can evaluate within the first 10 to 30 seconds from the start of imaging by the CT imaging module whether or not the ex-vivo tissue specimen is well positioned for further imaging. The imaging may be interrupted if necessary at this stage. The motion system 18 then moves the tissue specimen receiving element from the CT imaging module 11 to the PET imaging module 10 in an upward movement. Then the PET imaging module performs imaging of the ex-vivo tissue specimen. The image reconstruction module can then perform image reconstruction of the PET images. Reconstructed 3D PET and CT images can then be displayed separately and/or simultaneously on the display 4 for evaluation by the surgeon and/or nurse or by any other medical practitioner. The entire procedure from insertion of the ex-vivo tissue specimen into the image apparatus 1 until display of the CT and PET images preferably takes less than 20 minutes, more preferably less than 15 minutes, such that high precision margin assessment of the ex-vivo tissue specimen can be performed intraoperatively.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. An imaging apparatus for imaging ex-vivo tissue specimens comprising:
   a positron emission tomography (PET) imaging module including at least one pair of PET detectors;

a computed tomography (CT) imaging module including an X-ray source and an X-ray detector;

a tissue specimen receiving element configured to receive the tissue specimen to be imaged;

a motion system configured to move the tissue specimen receiving element from the CT imaging module to the PET imaging module;

wherein the PET imaging module is located above or beneath the CT imaging module.

2. The imaging apparatus according to claim 1, wherein a top side of the imaging apparatus includes an opening configured to allow loading of the tissue specimen on the tissue specimen receiving element, said opening being closeable by a lid.

3. The imaging apparatus according to claim 2, wherein the lid includes a camera configured to provide top view images of the tissue specimen receiving element.

4. The imaging apparatus according to claim 1, comprising a substantially vertical bore configured to receive the tissue specimen receiving element and allowing movement of the tissue specimen receiving element within the substantially vertical bore.

5. The imaging apparatus according to claim 1, wherein the motion system is configured to allow substantially vertical movement and/or rotational movement around a substantially vertical axis of the tissue specimen receiving element.

6. The imaging apparatus according to claim 1, wherein the motion system includes a kinematic mount.

7. The imaging apparatus according to claim 1, wherein the motion system is configured to perform a settling movement on the tissue specimen receiving element.

8. The imaging apparatus according to claim 1, wherein the PET imaging module is a high-resolution PET imaging module having a spatial resolution below 3 mm.

9. The imaging apparatus according to claim 1, wherein the CT imaging module is a micro-CT imaging module having a spatial resolution below 0.2 mm.

10. The imaging apparatus according to claim 1, wherein a shielding of the CT imaging module is a lead-free shielding.

11. The imaging apparatus according to claim 1, further comprising an image reconstruction module configured to perform image reconstruction based on data from the PET imaging module and/or from the CT imaging module.

12. The imaging apparatus according to claim 11, wherein the image reconstruction module is configured to perform 3D image reconstruction.

13. The imaging apparatus according to claim 1, further comprising a user interface.

14. The imaging apparatus according to claim 1, wherein the imaging apparatus is a mobile apparatus.

15. A method to perform ex-vivo tissue specimens imaging comprising the steps of:

providing an imaging apparatus according to claim 1;

providing the ex-vivo tissue specimen to be imaged to the tissue specimen receiving element;

optionally, the motion system performing a shaking movement on the tissue specimen receiving element;

the CT imaging module imaging the ex-vivo tissue specimen;

the PET imaging module imaging the ex-vivo tissue specimen;

wherein the motion system moves the tissue specimen receiving element from the CT imaging module to the PET imaging module in an upward or downward movement.

* * * * *